US 6,749,625 B2

(12) United States Patent
Pompa et al.

(10) Patent No.: US 6,749,625 B2
(45) Date of Patent: Jun. 15, 2004

(54) INTRAVASCULAR TEMPERATURE CONTROL CATHETER

(75) Inventors: Hortensia Pompa, San Clemente, CA (US); Nora Tran Pham, Lake Forest, CA (US); Lynn Miyeko Shimada, Orange, CA (US); Peter Barker, Oceanside, CA (US)

(73) Assignee: Alsius Corporation, Irvine, CA (US)

( * ) Notice: Subject to any disclaimer, the term of this patent is extended or adjusted under 35 U.S.C. 154(b) by 104 days.

(21) Appl. No.: 10/234,084

(22) Filed: Aug. 30, 2002

(65) Prior Publication Data

US 2004/0044387 A1 Mar. 4, 2004

(51) Int. Cl.[7] .................................................. A61F 7/00

(52) U.S. Cl. ........................ 607/105; 607/104; 607/106

(58) Field of Search .................................. 607/104–107

(56) References Cited

U.S. PATENT DOCUMENTS

| 6,264,679 B1 | 7/2001 | Keller et al. ................. 607/105 |
| 6,475,231 B2 | 11/2002 | Dobak, III et al. ......... 607/105 |
| 6,482,226 B1 | 11/2002 | Dobak, III ................... 607/104 |

*Primary Examiner*—Roy D. Gibson
(74) *Attorney, Agent, or Firm*—John L. Rogitz

(57) ABSTRACT

Various intravascular heat exchange catheters are disclosed that have non-straight heat exchange elements.

21 Claims, 2 Drawing Sheets

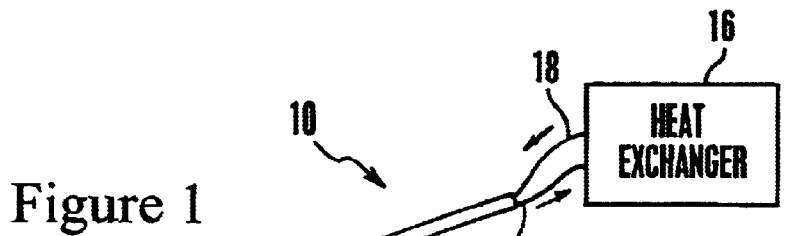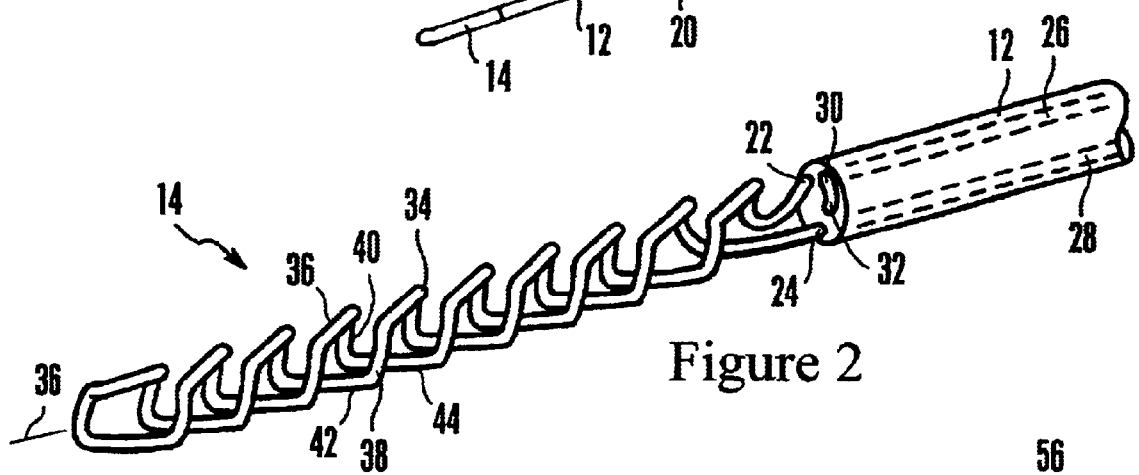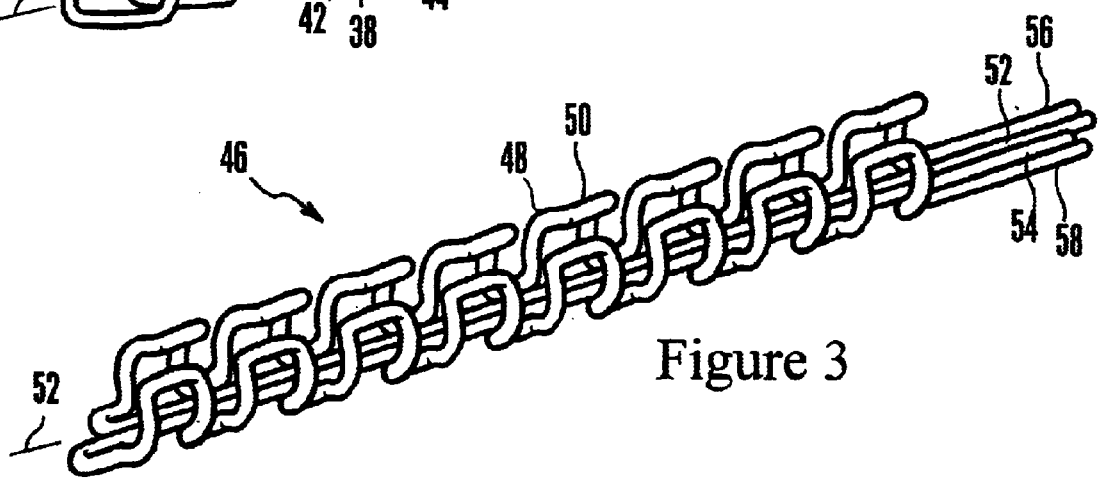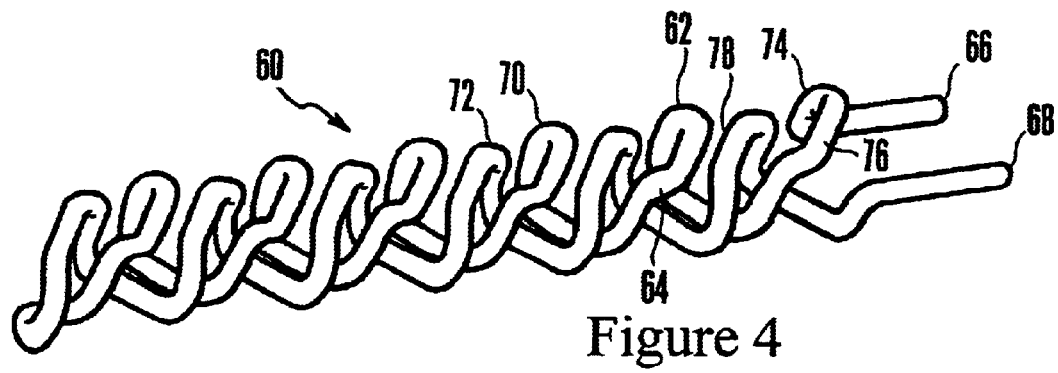

INTRAVASCULAR TEMPERATURE CONTROL CATHETER

FIELD OF THE INVENTION

The invention relates to intravascular catheters that can be used to control patient temperature.

BACKGROUND OF THE INVENTION

Intravascular catheters have been introduced for controlling patient temperature. Typically, a coolant such as saline is circulated through an intravascular heat exchange catheter, which is positioned in the patient's bloodstream, to cool or heat the blood as appropriate for the patient's condition. The coolant is warmed or cooled by a computer-controlled heat exchanger that is external to the patient and that is in fluid communication with the catheter.

For example, intravascular heat exchange catheters can be used to combat potentially harmful fever in patients suffering from neurological and cardiac conditions such as stroke, subarachnoid hemorrhage, intracerebral hemorrhage, cardiac arrest, and acute myocardial infarction, or to induce therapeutic hypothermia in such patients. Further, such catheters can be used to rewarm patients after, e.g., cardiac surgery or for other reasons. Intravascular catheters afford advantages over external methods of cooling and warming, including more precise temperature control and more convenience on the part of medical personnel.

The following U.S. patents, all of which are incorporated herein by reference, disclose various intravascular catheters/systems/methods: U.S. Pat. Nos. 6,419,643, 6,416,533, 6,409,747, 6,405,080, 6,393,320, 6,368,304, 6,338,727, 6,299,599, 6,290,717, 6,287,326, 6,165,207, 6,149,670, 6,146,411, 6,126,684, 6,306,161, 6,264,679, 6,231,594, 6,149,676, 6,149,673, 6,110,168, 5,989,238, 5,879,329, 5,837,003, 6,383,210, 6,379,378, 6,364,899, 6,325,818, 6,312,452, 6,261,312, 6,254,626, 6,251,130, 6,251,129, 6,245,095, 6,238,428, 6,235,048, 6,231,595, 6,224,624, 6,149,677, 6,096,068, 6,042,559.

Because it is sometimes desirable that a patient's temperature be changed to a desired value as rapidly as possible, the present invention recognizes the need to provide an intravascular heat exchange that has a relatively large cooling and/or rewarming capacity.

SUMMARY OF THE INVENTION

A heat exchange catheter includes a body, a coolant supply lumen in the body, and a coolant return lumen in the body. A heat exchange element communicates with the lumens and is configured for placement within a blood vessel of a patient such that blood can flow past the heat exchange element. Coolant is circulated through the body in a closed loop. In one embodiment, the heat exchange element includes longitudinally-spaced, generally square-shaped links when coolant flows through the catheter.

In a preferred non-limiting embodiment, the heat exchange element includes at least first, second, third, and fourth links in sequence, and coolant flows in a proximal to distal direction through the first and third links and in a distal to proximal direction through the second and fourth links. In an exemplary non-limiting embodiment each link defines a generally straight top defining opposed ends and two generally straight legs extending away from the top. Also, a connector segment may connect a leg of one link with a leg of another link. The links may be transversely oriented, i.e., the top of each link can be generally perpendicular to the axis of the catheter. However, in another non-limiting square link embodiment, the top of each link can be generally parallel to a long axis of the catheter. Thus, the links in this embodiment are longitudinally oriented and can be arranged in two sets. The tops of a first set of links are generally colinear with each other and the tops of a second set of links are generally colinear with each other, with the tops of the first set of links being generally parallel to and spaced from the tops of the second set of links.

In another aspect, the heat exchange element includes plural longitudinally-spaced links when coolant flows through the catheter, with each link being configured to establish a single coolant path that directs coolant through the link in a proximal to distal direction for at least a first part of the path and in a distal to proximal direction for at least a second part of the path. This embodiment can include meshed square links or curved, somewhat serpentine-shaped links in which coolant in the first part of the link flows generally up and proximally, and coolant in the second part of the link flows generally down and distally.

In still another aspect, the heat exchange element includes plural longitudinally-spaced links establishing a Venus flytrap configuration when coolant flows through the catheter.

The details of the present invention, both as to its structure and operation, can best be understood in reference to the accompanying drawings, in which like reference numerals refer to like parts, and in which:

BRIEF DESCRIPTION OF THE DRAWINGS

FIG. 1 is a schematic view of the present catheter operably engaged with a heat exchanger system;

FIG. 2 is a perspective view of a first heat exchange element, showing transverse-oriented square links, with portions of the catheter body broken away;

FIG. 3 is a perspective view of a second heat exchange element, showing longitudinally-oriented square links;

FIG. 4 is a perspective view of a third heat exchange element, showing convoluted square links;

DETAILED DESCRIPTION OF THE PREFERRED EMBODIMENT

Figure 5:
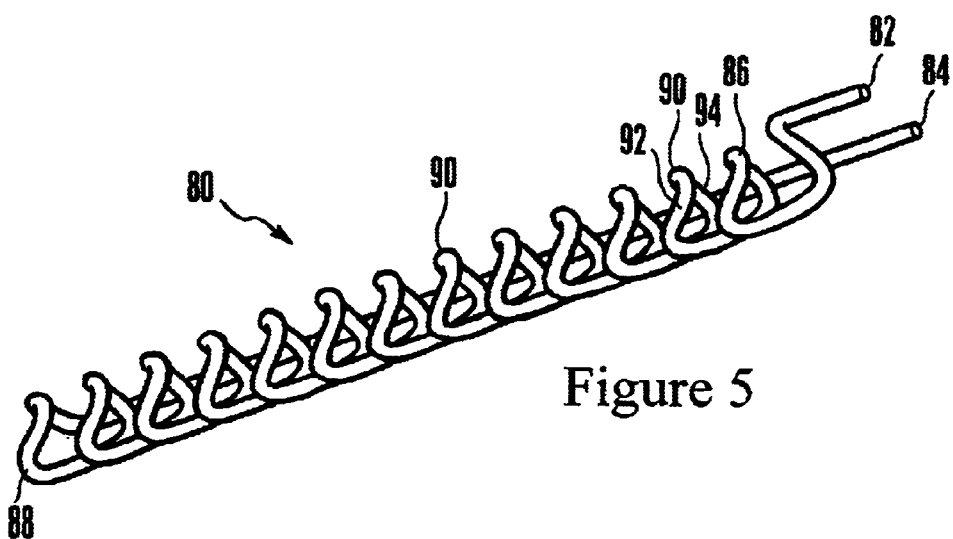
FIG. 5 is a perspective view of a fourth heat exchange element, showing serpentine links.

Referring initially to FIG. 1, an intravascular heat exchange catheter is shown, generally designated 10, that includes a tubular body 12 and a distal segment 14 that establishes a heat exchange element. Coolant such as but not limited to saline is circulated through the catheter 10 in a closed loop to and from a heat exchanger 16 through coolant supply and return tubes 18, 20 to heat or cool the coolant as desired to warm or cool a patient. The catheter 10 is made of biocompatible material that may be coated with an anti-coagulant substance such as Heperin®. Preferably, the catheter body 12 is made of flexible plastic, with the heat exchange element 14 being made of inflatable and deflatable medical balloon material, although the present heat exchange element principles apply to, e.g., metal structures as well.

In any case, the catheter 10 is sized to fit within the patient's bloodstream without blocking blood flow and without allowing coolant to enter the bloodstream. The blood can flow around substantially all of the exposed surface areas of the heat exchange elements disclosed below when the catheter 10 is positioned in the bloodstream and coolant is being circulated through the catheter, to exchange heat with the blood. In a preferred embodiment, the catheter 10 is configured for placement within the venous system, preferably in the superior vena cava or inferior vena cava through the jugular vein or subclavian vein or femoral vein. Less preferably the catheter 10 may be positioned in the arterial system.

Preferred non-limiting uses for the catheter 10 include inducing mild or moderate therapeutic hypothermia in patients suffering a cardiac arrest, acute myocardial infarction, stroke, brain trauma, or undergoing aneurysm surgery. The catheter 10 may also be used to rewarm such patients as well as rewarm patients post-surgery, e.g., post-cardiac bypass surgery.

Now referring to FIG. 2, the preferred catheter body 12 includes a coolant supply lumen 22, a coolant return lumen 24, and one or more (only two shown for clarity) infusion lumens 26, 28 that terminate in respective discharge ports 30, 32 for infusing medicament into a patient's bloodstream or for withdrawing or sampling blood from the patient. While the ports 30, 32 are shown located close together, they may be longitudinally spaced from each other and/or located in the tubular side of the catheter body.

As shown in FIG. 1, a first embodiment of the heat exchange element 14 includes longitudinally-spaced generally square-shaped links 34 that assume the square shape shown in FIG. 2 when coolant flows through the catheter, i.e., when the links are inflated. By "square shape" is meant that a link has at least three sides configured in a rectilinear configuration, with the legs discussed below being oriented more or less parallel to each other and generally perpendicular to the below-discussed link top from which they depend.

In the embodiment shown in FIG. 2, the links are longitudinally in sequence and transversely-oriented, i.e., a straight hollow top 36 of each link 36 is oriented above and perpendicular to the ling axis 36 of the catheter 10. Each link 34 also includes two hollow legs 38, 40 made integrally with the top 36 and extending downwardly from opposite ends of the top 36. The opposite ends of the legs 38, 40 are connected to or made integrally with connector segments 42, 44, with each connector segment 42, 44 connecting a leg of one link 34 with a leg of another link as shown to establish the heat exchange element 14. It is to be understood that terms of relative orientation such as "top", "above", "below" are used for convenience of disclosure, and do not necessarily indicate any orientation regarding catheter placement during heating or cooling. "Distal" and "proximal", however, are with respect to the catheter 10 when it is operationally positioned in the patient.

It can be appreciated in reference to FIG. 2 that coolant flows in a proximal to distal direction through every other link, and in a distal to proximal direction through the remaining links. That is, every other link can be thought of as a coolant supply link, and the links between the coolant supply links can be thought of as coolant return links. However, if desired coolant can flow in the same direction (either toward distal or toward proximal) through all links, with a straight tube connecting the distal-most link with the appropriate supply or return lumen 22, 24 in the catheter body 12.

In contrast to FIG. 2, FIG. 3 shows a heat exchange element 46 having two parallel sets of longitudinally-oriented generally square links 48 that can be connected to the catheter body 12 discussed above. As shown, the top 50 of each link 48 is generally parallel to the long axis 52 of the catheter, with the tops 50 in one set of links 48 being generally colinear with each other and with the tops 50 of the opposite set of links 48 being generally colinear with each other and generally parallel to and spaced from the tops 50 of the other set. If desired, the tops of the two sets can be positioned more closely together by forming inward bends in the legs of the links.

FIG. 3 shows that coolant flows through the links 48 of a set in one direction, preferably proximal to distal (although the opposite flow can be used), with coolant paths in the opposite direction for the sets being provided by respective return tubes 52, 54. Accordingly, link set extension tubes 56, 58 can be connected to the coolant supply lumen 22 of the catheter body 12 to establish fluid communication to the links, while the return tubes 52, 54 can be connected to the coolant return lumen 24. It is to be understood, however, that if desired the return tubes 52, 54 can be eliminated, and the distal-most link in one set can be connected to the distal-most link in the other set. In this case, one of the set extension tubes 56, 58 is connected to the coolant supply lumen 22 of the catheter body and the other tube 58, 56 is connected to the coolant return lumen.

FIG. 4 shows a heat exchange element 60 having generally square-shaped links 62 that are meshed with each other and that have slightly convoluted link connector segments 64. The links 62 are arranged in a coolant supply set of links and a coolant return set of links, and links in the supply set are staggered with links in the return set. An extension tube 66 of the supply set is connected to the coolant supply lumen 22 and an extension tube 68 of the return set is connected to the coolant return lumen 24, although each set of links could have its own return (or supply) tube in the manner of the heat exchange element 46 shown in FIG. 2. Because of the convolutions of the connector segments 64, the tops 70 of the links of the supply set form a slight angle with respect to the long axis of the catheter, while the tops 72 of the links of the return set form the same angle with respect to the long axis of the catheter but on the opposite side of the axis as shown.

As can be appreciated looking at FIG. 4, the cooperation of structure between the angled tops 70, 72 and slightly convoluted connector segments 64 of the links 62 ensures that each link 62 has a single coolant path that directs coolant through the link in a proximal to distal direction for at least a first part of the path and in a distal to proximal direction for at least a second part of the path. To illustrate, taking the first link in the coolant supply set (the upper right-most link shown in FIG. 4), coolant flows generally upwardly and in a distal-to-proximal direction through a segment 74, then generally downwardly and in a proximal-to-distal direction through a segment 76. It is possible, however, to configure the heat exchange element 60 for the opposite flow, i.e., coolant can flow generally downwardly and in a distal-to-proximal direction through a first link segment and generally upwardly and in a proximal-to-distal direction through a second segment of the same link.

FIG. 5 shows a heat exchange element 80 that can be connected to the coolant supply and return lumens 22, 24 of the catheter body 12 using supply and return tubes 82, 84. The supply tube 82 is connected to a first link 86, and the return tube 84 extends the length of the heat exchange element 80 and is connected to the last link 88. It is to be understood that coolant flow through the heat exchange element 80 can be in the opposite direction if desired.

As shown in FIG. 5, the links of the heat exchange element 80 are serpentine-shaped. Specifically, each link forms a gently curved flowpath throughout the link such that coolant flows through the link in a proximal to distal direction for at least a first part 90 of the link and in a distal to proximal direction for at least second parts 92, 94 of the link, with the second parts 92, 94 being on opposite sides of the first part 90 in the exemplary embodiment shown. Moreover, if desired the links can be configured such that coolant in one second part 92 flows generally up and proximally, and coolant in the other second part 94 flows generally down and proximally.

Figure 6:
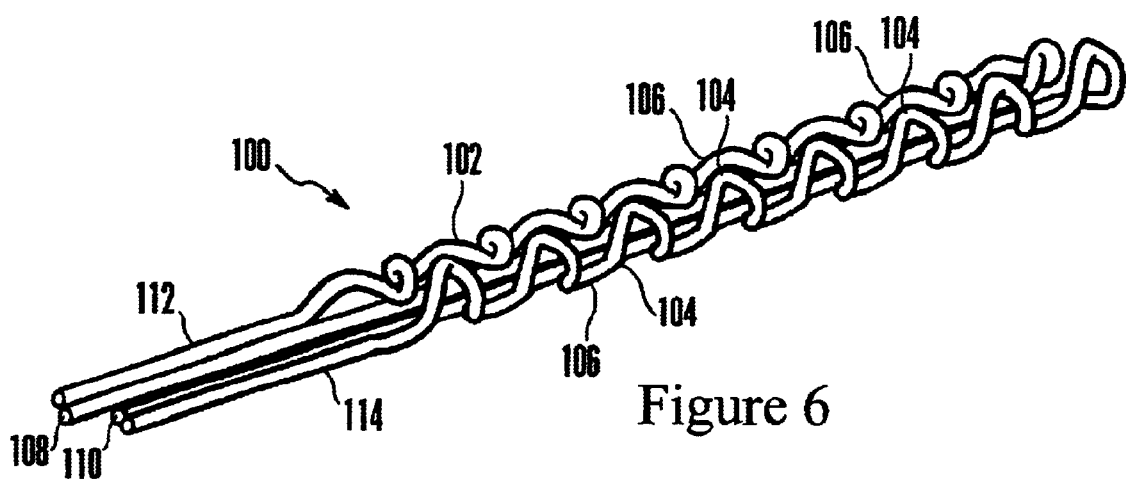
FIG. 6 is a perspective view of a fifth heat exchange element, showing Venus flytrap-like links.

FIG. 6 shows a heat exchange element that includes longitudinally-spaced links 102 establishing a Venus flytrap configuration when coolant flows through the catheter. More specifically, the heat exchange element 100 includes first and second sets of links 102 that extend along the length of the heat exchange element 100, with each link defining a convex bend 104 and with a concave recess 106 being established between successive bends 104 of links 102 in a set. As FIG. 6 shows, the bends 104 of the links 102 in each set are disposed in the recesses 106 of the opposite set when coolant flows through the catheter.

As was the case with the heat exchange element 46 shown in FIG. 3, in the heat exchange element 100 shown in FIG. 6 coolant can flow through the links 102 of a set in one direction, preferably proximal to distal (although the opposite flow can be used), with coolant paths in the opposite direction for the sets being provided by respective return tubes 108, 110. Accordingly, link set extension tubes 112, 114 can be connected to the coolant supply lumen 22 of the catheter body 12 to establish fluid communication to the links, while the set return tubes 108, 110 can be connected to the coolant return lumen 24. It is to be understood, however, that if desired the set return tubes 108, 110 can be eliminated, and the distal-most link in one set can be connected to the distal-most link in the other set. In this case, one of the set extension tubes 112, 114 is connected to the coolant supply lumen 22 of the catheter body and the other tube 114, 112 is connected to the coolant return lumen.

While the particular INTRAVASCULAR TEMPERATURE CONTROL CATHETER as herein shown and described in detail is fully capable of attaining the above-described objects of the invention, it is to be understood that it is the presently preferred embodiment of the present invention and is thus representative of the subject matter which is broadly contemplated by the present invention, that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more". All structural and functional equivalents to the elements of the above-described preferred embodiment that are known or later come to be known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. §112, sixth paragraph, unless the element is expressly recited using the phrase "means for" or, in the case of a method claim, the element is recited as a "step" instead of an "act".

What is claimed is:

1. A heat exchange catheter, comprising:

a body;

at least one coolant supply lumen and at least one coolant return lumen in the body; and at least one heat exchange element communicating with the lumens and configured for placement within a blood vessel of a patient such that blood can flow past the heat exchange element, wherein coolant is circulated through the body in a closed loop, the heat exchange element including plural longitudinally-spaced generally square-shaped links at least when coolant flows through the catheter.

2. The catheter of claim 1, wherein the heat exchange element includes at least first, second, third, and fourth links in sequence, wherein coolant flows in a proximal to distal direction through the first and third links and in a distal to proximal direction through the second and fourth links.

3. The catheter of claim 2, wherein the top of each link is generally parallel to a long axis of the catheter, the tops of a first set of links being generally colinear with each other and the tops of a second set of links being generally colinear with each other, the tops of the first set of links being generally parallel to the tops of the second set of links.

4. The catheter of claim 3, wherein the first set of links is a coolant supply being generally colinear with each other and the tops of a second set of links being generally colinear with each other, the tops of the first set of links being generally parallel to and spaced from the tops of the second set of links.

5. The catheter of claim 2, wherein the top of each link is generally perpendicular to a long axis of the catheter.

6. The catheter of claim 1, wherein each link defines a generally straight top defining opposed ends and two generally straight legs extending away from the top.

7. The catheter of claim 6, further comprising at least one connector segment connecting a leg of one link with a leg of another link.

8. The catheter of claim 1, wherein the heat exchange element establishes a distal portion of the body.

9. The catheter of claim 8, further comprising at least one infusion lumen in the body and communicating with at least one discharge port for infusing medicament into a patient's bloodstream.

10. The catheter of claim 9, wherein the heat exchange element is made of a balloon material.

11. A heat exchange catheter, comprising:

a body;

at least one coolant supply lumen and at least one coolant return lumen in the body; and at least one heat exchange element communicating with the lumens and configured for placement within a blood vessel of a patient such that blood can flow past the heat exchange element, wherein coolant is circulated through the body in a closed loop, the heat exchange element including plural longitudinally-spaced links at least when coolant flows through the catheter, each link being configured to establish a single coolant path through the link that directs coolant through the link in a proximal to distal direction for at least a first part of the path and in a distal to proximal direction for at least a second part of the path.

12. The catheter of claim 11, wherein coolant in the first part of the path flows generally up and proximally, and coolant in the second part of the path flows generally down and distally.

13. The catheter of claim 11, wherein the links are serpentine-shaped.

14. The catheter of claim 11, further comprising at least one infusion lumen in the body and communicating with at least one discharge port for infusing medicament into a patient's bloodstream.

15. The catheter of claim 14, wherein the heat exchange element is made of a balloon material.

16. The catheter of claim 11, wherein coolant in the first part of the path flows generally down and proximally, and coolant in the second part of the path flows generally up and distally.

17. A heat exchange catheter, comprising:
a body;
at least one coolant supply lumen and at least one coolant return lumen in the body; and
at least one heat exchange element communicating with the lumens and configured for placement within a blood vessel of a patient such that blood can flow past the heat exchange element, wherein coolant is circulated through the body in a closed loop, the heat exchange element including plural longitudinally-spaced links establishing a Venus flytrap configuration when coolant flows through the catheter.

18. The catheter of claim 17, comprising first and second sets of links extending along the length of the heat exchange element, each link defining at least one convex bend, a concave recess being established between successive bends of links in a set, the bends of the links in each set being disposed in the recesses of the opposite set when coolant flows through the catheter.

19. The catheter of claim 18, further comprising at least one infusion lumen in the body and communicating with at least one discharge port for infusing medicament into a patient's bloodstream.

20. The catheter of claim 17, wherein the heat exchange element establishes a distal portion of the body.

21. The catheter of claim 17, wherein the heat exchange element is made of a balloon material.

* * * * *